(12) United States Patent
Daffurn

(10) Patent No.: US 6,953,339 B1
(45) Date of Patent: Oct. 11, 2005

(54) TIP FOR DENTAL CURING LIGHT

(76) Inventor: Richard L. Daffurn, 1800 Thornsberry Rd., Sonoma, CA (US) 94576

( * ) Notice: Subject to any disclaimer, the term of this patent is extended or adjusted under 35 U.S.C. 154(b) by 55 days.

(21) Appl. No.: 10/146,448

(22) Filed: May 14, 2002

(51) Int. Cl.[7] .............................................. A61C 3/00
(52) U.S. Cl. ..................................................... 433/29
(58) Field of Search .................. 433/29, 215, 141 OR, 433/163, 172, 173, 174, 175, 176; 206/63.5, 206/368; 81/436

(56) References Cited

U.S. PATENT DOCUMENTS

| | | | |
|---|---|---|---|
| 4,666,405 A | | 5/1987 | Ericson ....................... 433/229 |
| 5,017,140 A | | 5/1991 | Ascher ........................ 433/215 |
| 5,290,169 A | * | 3/1994 | Friedman et al. ............. 433/29 |
| 5,312,249 A | * | 5/1994 | Kennedy ...................... 433/29 |
| 5,328,368 A | * | 7/1994 | Lansing et al. ............... 433/29 |
| 5,759,032 A | * | 6/1998 | Bartel .......................... 433/29 |
| 5,791,898 A | | 8/1998 | Maissami .................... 433/164 |
| 5,971,755 A | * | 10/1999 | Lieberman et al. ............ 433/29 |
| 6,033,223 A | | 3/2000 | Narusawa et al. .......... 433/226 |
| 6,186,786 B1 | | 2/2001 | Trushkowsky .............. 433/164 |
| 6,208,788 B1 | | 3/2001 | Nosov ........................ 385/121 |
| 6,280,187 B1 | * | 8/2001 | Slone .......................... 433/29 |

\* cited by examiner

*Primary Examiner*—John J Wilson
(74) *Attorney, Agent, or Firm*—Scott W. Hewett

(57) ABSTRACT

An optic tip for use with a dental curing lamp has a convex lens extending across the bottom of the mounting cup. The curing tip is a half-obloid that creates a secondary void with a compound curve in the cured filling material. The secondary void provides greater bonding area for the secondary filling material and the secondary filling material creates a contact point with the adjacent tooth. In a particular embodiment, the optic tip extends not more than 6 mm from the end of the curing wand, facilitating operation in the patient's mouth compared to larger devices. The depth of the secondary void is also self-limiting by the desirably short curing tip, allowing the dentist to cure the primary filling material without having to watch the depth of the curing tip.

15 Claims, 3 Drawing Sheets

TIP FOR DENTAL CURING LIGHT

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

The present invention relates generally to devices for curing light-hardening polymer dental filling material, and more particularly to a focusing tip configured to be attached to the end of a dental curing light.

Light-hardening polymer dental material has enjoyed wide success in providing a dental filling material that is the same or nearly the same color as the patient's tooth. Fillings made with the naturally colored resin are less noticeable, compared to similar amalgam-type fillings. However, amalgam fillings continue to be used in some instances, such as on posterior teeth (i.e. bicuspids and molars) where the cosmetic detraction of the amalgam filling is less noticeable.

Dental amalgam is a mechanical mixture of mercury and powdered silver alloy. The firm consistency of dental amalgam makes restorations relatively easy to place, to form tight contacts, and to provide tight margins. Dental amalgam provides excellent wear and has a proven record of biological compatibility.

Filling material is generally pressed into a cavity prepared by the dentist. If a portion of the cavity is coextensive with a sidewall of the tooth, a matrix band is typically used to provide an outer surface when filling the cavity. The matrix band is a thin band of metal or plastic that the dentist tightens around the tooth being filled. It is resilient, and generally conforms to the perimeter of the tooth. Amalgam filling can be packed into the cavity and against the matrix band, and after the amalgam condenses, the matrix band is removed. The contact between the filled tooth and the adjacent tooth is preserved with amalgam filling material because the amalgam is firm and retains its shape after condensation.

Polymer-based filling material flows differently than amalgam and cannot be packed into a cavity in the same manner to condense in the shape defined by the matrix band. Light-cured fillings do not go through a gradual hardening phase during which they can be carved into a desired shape. They are too soft at placement and too hard after light hardening, whereas silver amalgam filling can be finished with hand carving instruments as they harden. Light-cured filling material is typically shaped after hardening with metal burs or fine diamond-coated burs.

Light-cured white fillings depend on a tight, hard bond with the tooth material, otherwise leakage and decay will result. The filling material should be fully cured, which can be difficult because the curing light might not completely penetrate thick fillings. However, the light-cured filling material can be built up in several layers with intermediate curing steps. It is similarly more difficult to use light-cured filling material to form contacts between teeth. Contacts are preferably tight, and open contacts allow foods to pass through while chewing, which gets stuck between the teeth. Food stuck between the teeth can be annoying, and can cause periodontal or gum problems.

Techniques have been developed to cure polymer-based filling by pressing the matrix band against the adjacent tooth while light curing the polymer filling material in the cavity. A small light-transmitting cone is pressed against the inside of the matrix band to hold it against the adjacent tooth. Sometimes, dental wedges are used to spread the teeth apart while the matrix band is placed and the cavity filled. This allows more filling material to be placed between the teeth. A second application of polymer filling material is then placed in the secondary cavity formed by the cone used to hold the matrix band against the adjacent tooth, and the second application of polymer filling material is light hardened. After removal of the wedge and matrix band, the teeth will return to their preoperative position and form a tight contact.

Unfortunately, conventional cones are relatively large, making them difficult to manipulate in a patient's mouth. This shortcoming is particularly noticeable when attempting to use light-cured filling material in posterior teeth. It is important to obtain a thorough cure of the resin in posterior teeth because of the pressures and stresses they must endure. Some conventional cones reduce the light intensity reaching the filling material, which requires the dentist to hold the light on the filling longer, further complicating the procedure. The cones also leave a straight-sided void in the first application of filling material, and some do not efficiently transmit light to the preparation region. Inefficient transmission of light to the filling material can result in incomplete hardening of the filling material for a given time, or require additional time in the patient's mouth. Thus, existing cones and similar devices have undesirable size, shape, and transmission characteristics.

BRIEF SUMMARY OF THE INVENTION

The present invention provides a compact optic tip for a dental curing light that delivers high-intensity light to the filling area. The tip shape creates a desirable doubly curved secondary void in the cured filling material to allow finishing the filling with well-bonded secondary filling material that creates a contact point.

In one embodiment, an optic tip for use with a dental curing lamp having a curing wand with a curing wand end has a mounting tip configured to receive the curing wand (typically 8 mm, 9 mm, 9.5 mm, or 12 mm in diameter). A convex lens surface extends across the inner diameter of the mounting cup and a curing tip portion has a non-reentrant half-obloid end. In a further embodiment, the point of the curing tip is not more than 10 mm from the curing wand end when the optic tip is mounted on the curing wand. In a yet further embodiment, the maximum curing tip diameter is less than 3.3 mm, allowing the dentist to insert the full length of the curing tip into the filling material.

DETAILED DESCRIPTION OF THE INVENTION

I. Prior Art Devices

Figure 1A:
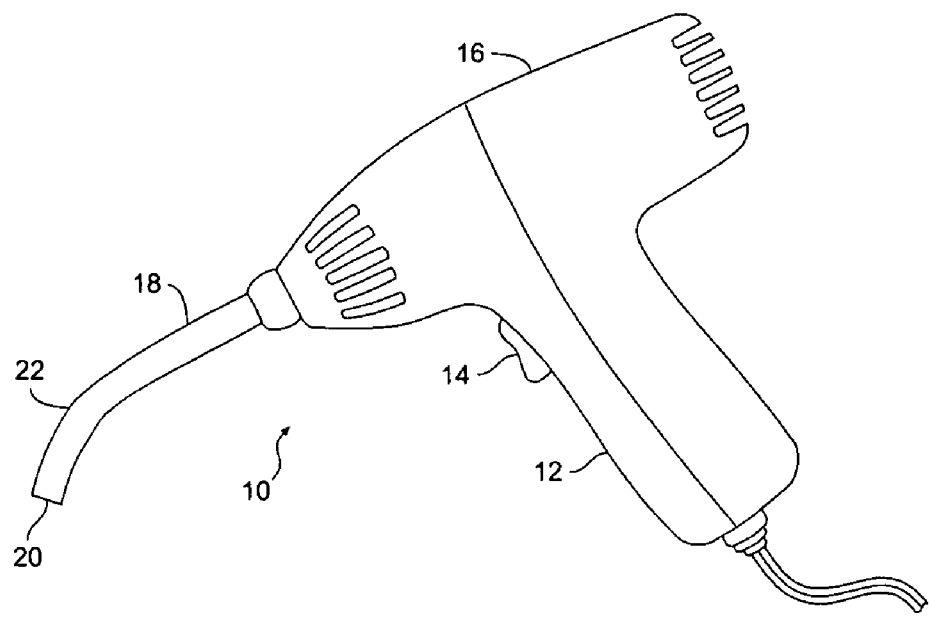
FIG. 1A is a simplified side view of a prior art dental curing light.

FIG. 1A is a simplified side view of a prior art dental curing light 10. Such lights have been in use for some time and are used to provide high-intensity light of selected wavelengths inside a patient's mouth. The dental curing light typically includes a handle 12 with a switch 14 that activates the light. In some instances, a timer is included so that depressing the switch turns the light on for a pre-selected period of time. A lamp (not shown) inside the housing 16 generates high-intensity light in the desired wavelengths. For example, some light hardening filling material hardens when exposed to light in the 400–600 nm range of the spectrum.

The dental curing light may include a wavelength-selective filter (not shown) between the lamp and the light pipe 18 to filter out non-selected wavelengths, such as heat-generating infrared wavelengths. The light pipe conveys light from the lamp to the end 20 of the light pipe. The light pipe is typically a bundle of optic fibers or glass rod with a coating that serves as a light conduit. The light pipe is also commonly known as a "curing wand" and may come in a variety of standard diameters, such as 8 mm, 9 mm, 9.5 mm, and 12 mm.

The curing wand typically has a slight bend 22 of about 30 degrees approximately 16 mm from the end 20 of the curing wand. Since the light must be directed into the mouth from this hand-held unit, this slight bend aids in placing the full surface of the rod end flush with the surface of the tooth to receive maximum exposure.

Figure 1B:
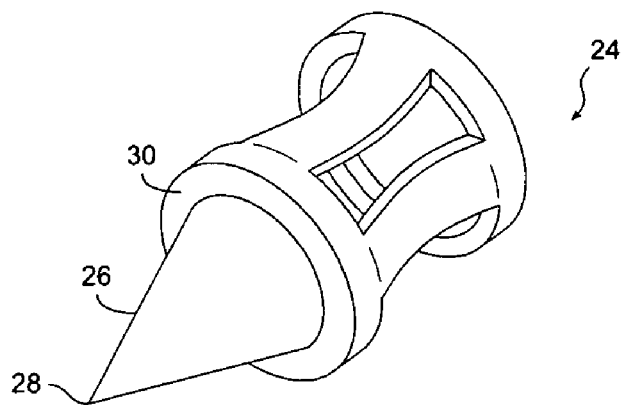
FIG. 1B is a simplified perspective view of a prior art light prism tip.

FIG. 1B is a simplified perspective view of a prior art light prism tip 24. Such tips are described in U.S. Pat. No. 5,791,898, issued Aug. 11, 1998 to Fari Maissami. The light prism tip is described as having a magnified prism, which is defined therein as being a transparent body that is bounded in part by two nonparallel faces. The light prism tip is used to disperse a beam of light, and has the power or capability of causing the light to become more intense. The tip portion 26 has a conical or elliptical (not illustrated) shape extending in generally a straight line from the point 28 to the face 30 of the light prism tip. A product known as FOCU-TIP™ available from HAGAR WORLDWIDE, of Odessa, Fla., appears to be manufactured in accordance with this patent. A sample FOCU-TIP sold for use with an 8 mm curing wand had the point 28 of the tip extending approximately 10 mm from the end of the curing wand.

Figure 1C:
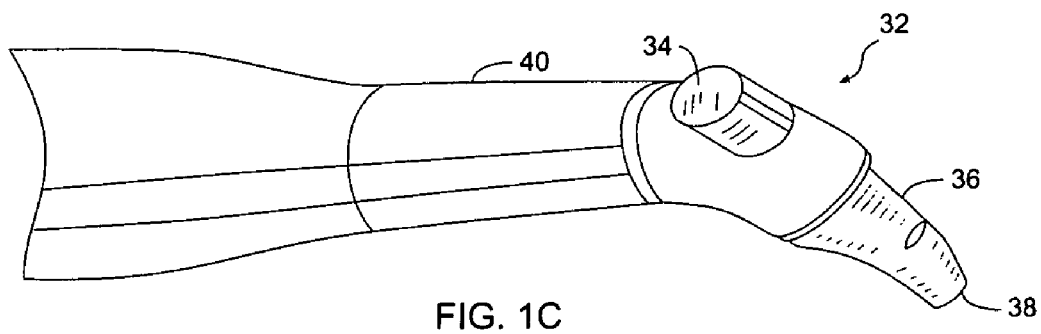
FIG. 1C is a simplified perspective view of a prior art dental wand instrument.

FIG. 1C is a simplified perspective view of a prior art dental wand instrument 32. Such dental instruments are described in U.S. Pat. No. 6,186,786. A dental instrument known and commercially available as TRI-MAX™ appears to be manufactured in accordance with this patent. A sample of a TRI-MAX instrument measured approximately 16 mm from the upper face 34 of the clear insert 36 to the lower tip 38 of the clear insert. The end of the curing wand is generally placed against the upper face 34 of the clear insert, which conducts the light to the curing region. The clear insert is placed in a handle 40, which allows the dentist to manipulate the instrument independently of the curing light.

II. Specific Embodiments of the Present Invention

Figure 2:
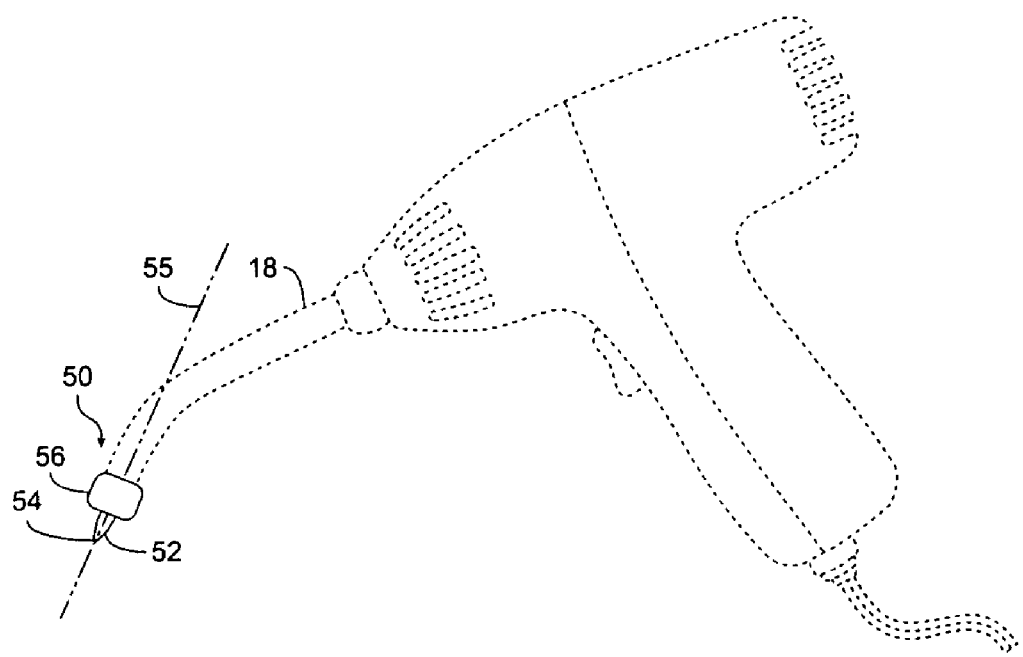
FIG. 2 is a simplified side view of an optic tip according to an embodiment of the present invention installed on a dental curing light.

FIG. 2 is a simplified side view of an optic tip 50 according to an embodiment of the present invention installed on a prior art dental curing light (shown in dashed lines). The optic tip includes a curing tip portion 52 that extends less than 10 mm from the end (see FIG. 1A, ref. num. 20) of the curing wand 18. In a further embodiment, the curing tip portion extends less than 6 mm from the end of the curing wand. In other words, the furthest point 54 of the curing tip portion 52 is not more than 6 mm from the end of the curing wand. In a yet further embodiment, the maximum diameter of the curing tip portion is not greater than about 2.3 mm.

The curing wand is shown as being essentially constant diameter; however, some curing wands are tapered, the diameter of the end nearer the light to be greater than the diameter of the curing end. The mounting cups of optic tips according to embodiments of the present invention might therefore also be tapered for mounting to tapered curing wands. Optical tips according to the present invention may also be used with other light sources. For example, the light illustrated in FIG. 1A includes a relatively broad-band bulb in the housing of the device, along with a cooling fan to remove excess heat that the bulb develops. Other optical light curing instruments use light-emitting diodes ("LED's"), which typically generate much less heat. LEDs can be chosen to emit light within the desired wavelength range, rather than generating light at many frequencies, and then filtering out the undesired wavelengths. An LED or array of LEDs can be mounted in a housing and the light conveyed to the optic tip through a light pipe or optic fiber bundle, or an LED or LED array might be mounted on the end of a curing wand, producing the light at the end of the wand.

These exemplary dimensions are sufficient for entry in many dental restorations, such box forms made with a type 557 bur. Larger or smaller variations could be produced for larger or smaller teeth, such as children's teeth. Contact points are typically desirable within 2 mm of the occlusal surface of the tooth, and no matter how much of the tooth is missing or removed in the preparation, the desired contact area about the same. The compact form allows the same tip to be used in a variety of circumstances, and allows the dentist to tip or draw the light wand instrument against neighboring tooth in the box form.

The compact nature of the optic tip achieves significant advantages for curing dental restorations. It allows the dentist to perform the procedure with less patient discomfort because the patient does not need to open her mouth as far as with other light curing tip devices. The curing tip portion is symmetrical about a central axis 55 (i.e. has radial symmetry), so that the dentist does not have to orient the curing light at a particular angle to the patient's teeth, and this symmetry also allows the tip to be rotated in the cured resin, unlike unsymmetrical tips, which might have to be tilted or twisted in order to be removed from the cured resin.

In embodiments in which the maximum diameter of the curing tip portion is less than about 2.3 mm, the dentist can fully insert the curing tip portion into the uncured filling material until the face 56 of the optic tip contact the patient's tooth. The dentist does not have to look into the patient's mouth and hold a dental instrument with a curing tip at a selected height in the patient's mouth while manipulating the dental curing light with his other hand to achieve appropriate insertion of the curing tip into the filling material. The obloid shaped taper of the optical tip allows use of the same size tip in a variety of cavity sizes. The optical tip on the light wand is inserted as far as possible into a suitably large preparation (box form), and tipped or drawn against the matrix band, and then the light is turned on for the selected period to cure the filling material.

The optic tip is preferably made of plastic material that is clear at the wavelengths of light used to cure the filling material, such as polystyrene, acrylics, clear polyolefins, or plastic alloys. Some suitable plastics are thermoplastics, such as polystyrene, that cannot be heat-sterilized, and thus it is desirable to provide disposable tips to avoid cross-patient contamination.

Polystyrene, and other suitable plastics, can be injection molded, which is a relatively inexpensive process that allows the manufacture of disposable optic tips. Injection molding also can produce optic tips with high surface-quality. High surface quality is desirable to avoid scattering and back-reflection of light, particularly in the convex lens portion, where the light enters the tip, and the curing tip portion, where the light exits the tip. Some plastics may be suitably durable to allow sterilization and hence be re-useable.

Figure 3:
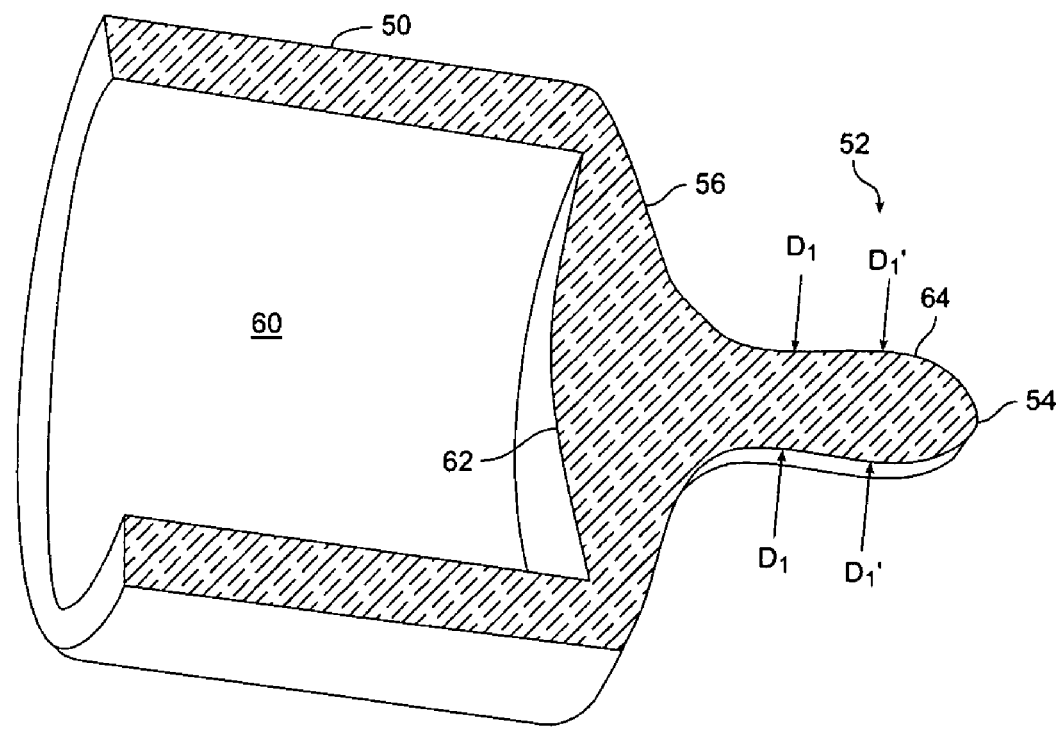
FIG. 3 is a simplified perspective cross section of an optic tip according to an embodiment of the present invention.

FIG. 3 is a simplified perspective cross section of an optic tip 50 according to an embodiment of the present invention. The optic tip includes a mounting cup 60 that fits over the end of the curing wand, and typically has an inside diameter nominally the same or slightly smaller than the outer diameter of the curing wand. The optic tip can come in a variety of sizes to fit standard curing wands. When the optic tip is mounted on a dental curing light, the optic tip covers the end of the curing wand.

The mounting cup includes a convex lens 62 extending across the entire inner diameter of the mounting cup 60. In other words, the inside bottom surface of the mounting cup forms a convex lens. The convex lens collimates or focuses the light as it exits the end of the curing wand into the curing tip portion 52. The tip is solid between the convex lens and the end of the curing tip portion. The curing tip portion then efficiently transmits this collected light beam into the depths of the filling material. The intensity of the light provided can shorten the procedure time, and in some instances eliminate the necessity of layering and curing multiple applications of material; however, another small portion of filling material is typically used to fill the secondary void left by the curing tip, compressed again by the optic tip and light cured. If another void is formed in the cured secondary filling material by the optic tip, it can usually be filled and cured with the curing wand without the optic tip. This technique provides a solid contact with the adjacent tooth.

The curing tip portion 52 has a section in a plane intersecting the central axis that is half-obloid 64, which creates a rounded, tapered secondary void. It is generally preferable that the curing tip portion has a radius that decreases from the curing wand end to the end 54 of the curing tip portion. This is to avoid having the curing tip from becoming stuck in the cured filling material. In the illustrated embodiment, the maximum diameter $D_1$ of the curing tip portion is constant for a short distance from the face 56 of the optic tip is about 2.3 mm. The diameter of the half obloid 64 decreases from the maximum diameter $D_1'$ (2.3 mm) to essentially a zero radius at the end 54 or point of the optic tip. The constant-diameter portion of the curing tip portion may be omitted or lengthened in other embodiments.

Another advantage of having a curing tip portion that is not undercut (ie. that could form a re-entrant void) is that it allows the optic tip to be injection molded. The half obloid creates a secondary void with one radius of curvature about the central axis, as with conventional conical tips, and another curve in a plane intersecting the central axis (ie. a half obloid that is round in a cross section perpendicular to the central axis). A secondary void with such a compound curved surface is easier to fill with secondary filling material and provides enhanced surface area for bonding the secondary filling material to the previously cured filling material. More particularly, the half-obloid void provides a more desirable broad surface area in the contact point against the neighboring tooth, compared to a sharp point, when the matrix band is removed. If a conventional conical optic tip is placed with its edge pressing against the matrix band, the point of tip will be adjacent to the matrix band and thus unsupported by cured resin on the outside of the tooth. The end of the void left by the half-obloid tip according to an embodiment of the present invention is typically removed from the contact point by about one half the diameter of the tip. This allows more of the first load of filling material to be cured in the contact region, forming a broad, rounded contact that keeps food out from between the teeth. In other words, the end of the optic tip is rounded over and is drawn away from the contact area in normal use.

In an alternative embodiment, the curing tip portion is a partially flattened half-obloid, thus it does not have radial symmetry about the central axis of the optical curing tip. The flattened shape can be inserted to form narrower secondary voids with even more surface area in the contact margin than a round obloid or conical point of similar volume. The flattened plane of the tip can be oriented by rotating the optical curing tip on the end of the curing wand.

Figure 4:
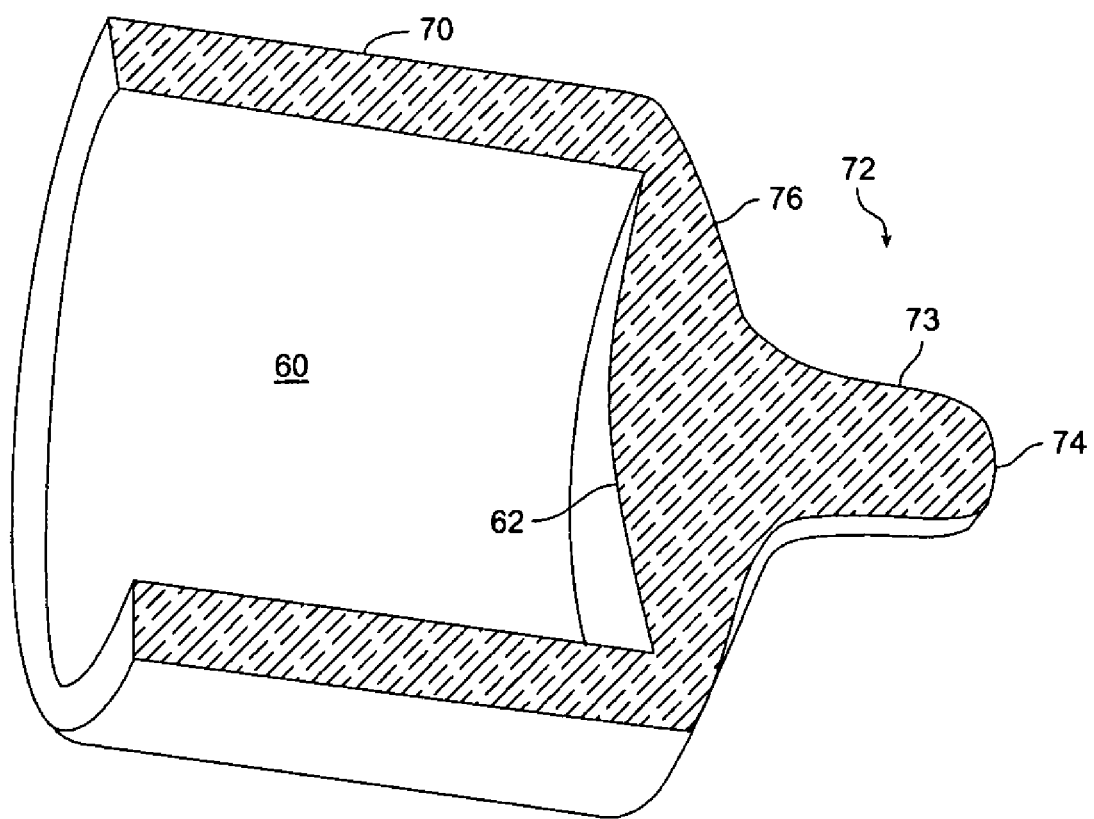
FIG. 4 is a simplified perspective cross section of an optic tip according to another embodiment of the present invention.

FIG. 4 is a simplified perspective cross section of an optic tip 70 according to another embodiment of the present invention. The optic tip includes a mounting cup 60 that fits over the end of the curing wand, and typically has an inside diameter nominally the same or slightly smaller than the outer diameter of the curing wand. The optic tip can come in a variety of sizes to fit standard curing wands. When the optic tip is mounted on a dental curing light, the optic tip covers the end of the curing wand.

The mounting cup includes a convex lens 62 extending across the entire inner diameter of the mounting cup 60. In other words, the inside bottom surface of the mounting cup forms a convex lens. The convex lens collimates or focuses the light as it exits the end of the curing wand into a curing tip portion 72. The tip is solid between the convex lens and the end of the curing tip portion. The curing tip portion then efficiently transmits this collected light beam into the depths of the filling material.

The curing tip portion 72 includes a cylindrical portion with a rounded end 74. The diameter of the cylindrical portion is generally less than 3.3 mm and in one embodiment is about 2.3 mm. The rounded end is illustrated as being essentially hemispherical, but could be ovoid, parabolic, conical, or other shape. As with the optic tip illustrated in FIG. 3, the cylindrical tip avoids becoming captivated in the cured filling material, and in typical operation the cylindrical portion is at least partially inserted into the filling material. The distance from the end 74 of the tip to the face 76 of the cup is less than about 10 mm, and in one embodiment is about 6 mm, and in another embodiment is less than about 6 mm.

III. Experimental Results

An optic tip according to an embodiment of the present invention was machined from plastic stock. An 8 mm FOCU-TIP™ and a TRI-MAX™ instrument were purchased from commercial sources. A standard dental curing light having an 8 mm curing wand was used in conjunction with a photometer supplied with the dental curing light. The photometer is regularly used to check the output of the dental curing light. Generally, if the output of the light is below a specified value, the bulb is replaced or the dental curing light otherwise serviced or repaired to insure that the light is sufficient for curing the filling material in the anticipated time.

The light pipe without any tip or intermediate device registered a value of 600 (arbitrary units) when the end of the curing wand was placed on the photometer. The FOCU-TIP registered a value of 179 when placed on the end of the curing wand and held with the point contacting the photometer in an essentially vertical fashion. The TRI-MAX recorded a value of 70 when placed between the end of the curing wand and against the photometer. In comparison, the tip fabricated according to an embodiment of the present invention, having a convex lens extending across the base of the mounting cup and a round half-obloid curing tip about 6 mm long and about 2 mm in maximum diameter recorded 271 light units when placed on the end of the curing wand and vertically against the photometer. This is significantly more light than is conveyed by the prior-art devices and is believed to provide superior curing of the filling material.

It is noteworthy that the tip fabricated according to the present invention was machined from stock, and that the machined surfaces of the tip were not highly polished. It is believed that polishing, such as "fire" polishing or diamond turning polishing, or other manufacturing methods, such as injection molding, will provide even higher light values.

While the invention has been described above with respect to specific embodiments, other embodiments may be apparent to those with ordinary skill in the art. Various details of the described embodiments of the invention may be changed without departing from the spirit or scope of the invention. Therefore, the foregoing description of the embodiments of the invention is provided for the purpose of illustration only, and not for the purpose of limiting the invention as defined by the appended claims and their equivalents.

What is claimed is:

1. An optic tip for use with a dental curing light having a curing wand with a curing wand end, the optic tip comprising:
    a mounting cup configured to fit over the curing wand end having
        an inner diameter configured to receive the curing wand end so as to removably attach the optic tip to the curing wand and
        a convex lens surface extending across the inner diameter of the mounting cup;
    a face; and
    a curing tip portion having
        a cylindrical portion proximate to and extending from the face with a diameter less than the inner diameter, and
        a rounded portion proximate to and extending from the cylindrical portion.

2. The optic tip of claim 1 wherein the rounded portion is a half-obloid portion.

3. The optic tip of claim 2 wherein half-obloid portion is flattened.

4. The optic tip of claim 1 wherein the rounded portion is at least partially flattened.

5. The optic tip of claim 4 wherein the rounded portion is hemispherical.

6. The optic tip of claim 1 wherein an end of the curing tip portion is not more than 10 mm from the curing wand end when the optic tip is mounted on the curing wand.

7. The optic tip of claim 1 wherein an end of the curing tip portion is not more than 6 mm from the curing wand end when the optic tip is mounted on the curing wand.

8. The optic tip of claim 1 wherein the diameter is not greater than 3.3 mm.

9. The optic tip of claim 1 wherein the inner diameter is selected from the group consisting of 8 mm, 9 mm, 9.5 mm, and 12 mm.

10. The optic tip of claim 1 wherein the mounting cup is tapered.

11. The optic tip of claim 1 wherein at least the convex lens surface and the curing tip portion comprise specular plastic transparent from about 450–550 nm.

12. The optic tip of claim 1 wherein the optic tip is fabricated from polystyrene.

13. The optic tip of claim 1 wherein the optic tip is fabricated from acrylic, poly-olefins, or plastic alloy.

14. An optic tip for use with a dental curing light having a curing wand with a curing wand end, the optic tip comprising:
    a mounting cup configured to fit over the curing wand end having
        an inner diameter configured to receive the curing wand end so as to
    removably attach the optic tip to the curing wand and
        a convex lens surface extending across the inner diameter of the mounting cup;
    a face; and
    a curing tip portion having a cylindrical portion proximate to and extending from the face with a diameter less than the inner diameter and not greater than 3.3 mm, and a non-reentrant half-obloid end proximate to and extending from the cylindrical portion with a point not more than 6 nm from the curing wand end when the optic tip is mounted on the curing wand.

15. An optic tip for use with a dental curing light having a curing wand with a curing wand end, the optic tip comprising:
    a mounting cup configured to fit over the curing wand end having
        an inner diameter configured to receive the curing wand end so as to removably attach the optic tip to the curing wand and
        a convex lens surface extending across the inner diameter of the mounting cup;
    a face; and
    a curing tip portion having a cylindrical portion with a diameter less than the inner diameter and not greater than 3.3 mm, and a rounded end portion extending not more than 6 mm from the curing wand end when the optic tip is mounted on the curing wand.

* * * * *